US008408052B2

(12) United States Patent
Pitkanen et al.

(10) Patent No.: US 8,408,052 B2
(45) Date of Patent: Apr. 2, 2013

(54) EQUIPMENT FOR CONCENTRATING AND ANALYZING COMPONENTS CONTAINED IN A FLOWING MEDIUM AND ANALYZING METHOD

(75) Inventors: Janne Petteri Pitkanen, Kuopio (FI); Tero Tapio Hannola, Vantaa (FI); Terhi Marjukka Mattila, Kuopio (FI)

(73) Assignee: Environics Oy (FI)

( * ) Notice: Subject to any disclaimer, the term of this patent is extended or adjusted under 35 U.S.C. 154(b) by 228 days.

(21) Appl. No.: 12/995,095

(22) PCT Filed: Jun. 1, 2009

(86) PCT No.: PCT/FI2009/050459
§ 371 (c)(1),
(2), (4) Date: Feb. 22, 2011

(87) PCT Pub. No.: WO2009/147294
PCT Pub. Date: Dec. 10, 2009

(65) Prior Publication Data
US 2011/0162443 A1    Jul. 7, 2011

(30) Foreign Application Priority Data

Feb. 6, 2008   (FI) ........................................ 20085532

(51) Int. Cl.
*G01N 5/02* (2006.01)
(52) U.S. Cl. ............................................. 73/73
(58) Field of Classification Search ........... 73/73
See application file for complete search history.

(56) References Cited

U.S. PATENT DOCUMENTS 4,019,021 A * 4/1977 Schladitz .................. 392/485

7,299,711 B1 * 11/2007 Linker et al. ............... 73/863.23
2002/0088344 A1 * 7/2002 Chmiel et al. .................. 95/148
2003/0075045 A1 * 4/2003 Cowles et al. ................. 95/148
2010/0242579 A1 * 9/2010 Tipler et al. ..................... 73/73

FOREIGN PATENT DOCUMENTS

| GB | 1423055 A | 1/1976 |
| WO | 96/09104 A1 | 3/1996 |
| WO | 96/09886 A1 | 4/1996 |
| WO | 96/09887 A1 | 4/1996 |

OTHER PUBLICATIONS

International Search Report for parent application PCT/FI2009/050459, having a mailing date of Sep. 8, 2009.
Finnish Office Action and Search Report for priority application FI 20085532, dated Jan. 13, 2009 and Jan. 12, 2009, respectively.

* cited by examiner

*Primary Examiner* — Lisa Caputo
*Assistant Examiner* — Jamel Williams
(74) *Attorney, Agent, or Firm* — Andrus, Sceales, Starke & Sawall, LLP

(57) ABSTRACT

The invention relates to equipment for concentrating and analyzing components contained in a flowing medium, and an analyzing method applying said equipment. The analyzing equipment comprises a concentrator, including a porous sorbent bed, in which components can be absorbed or adsorbed from the medium flow, said bed being electroconductive, so that components can be desorbed to a washing flow by heating the bed with electric current; and to an analyzer defining the desorbed components, said analyzer being for instance a gas detector. According to the invention, the sorbent bed is in the flowing direction widened towards its outlet end, having for example the shape of a truncated cone. By means of the invention, the temperature in the sorbent bed is equalized by transferring heat in the washing flow towards the bed outlet end, which end receives a weaker heating effect per unit of volume, owing to the widening shape of the bed.

17 Claims, 2 Drawing Sheets

EQUIPMENT FOR CONCENTRATING AND ANALYZING COMPONENTS CONTAINED IN A FLOWING MEDIUM AND ANALYZING METHOD

CROSS-REFERENCE TO RELATED APPLICATIONS

This application is the U.S. national stage application of International Application No. PCT/FI2009/050459, filed Jun. 1, 2009, which International application was published on Dec. 10, 2009, as International Publication No. WO 2009/147294A1 in the English language, which application is incorporated herein by reference. The International application claims priority of Finnish Patent Application No. 20085532, filed Jun. 2, 2008, which application is incorporated herein by reference.

BACKGROUND

The invention relates to a device for concentrating the components contained in a flowing medium, which device is provided with inlet and outlet ends for an axial flow, as well as with a porous sorbent bed arranged therebetween, in which bed components can be absorbed or adsorbed from the medium flow conducted through the bed, said bed being electroconductive, so that the components can be desorbed to a washing flow conducted through the bed by heating the bed with an axially oriented electric current. In addition, the invention relates to equipment for analyzing components contained in a flowing medium, said equipment comprising, apart from a sorbent bed absorbing or adsorbing components, an analyzer that is in flowing communication with the bed, for defining the components desorbed from the bed, as well as an analyzing method for applying the described analyzing equipment.

The publication WO 96/09887 describes an adsorber that is meant for cleaning a flowing medium of impurities contained therein, and for separating different impurities from each other. The device comprises a sorbent bed made of activated carbon, through which a flow is arranged to pass, as well as electrodes provided at the sides of the bed for heating the bed by electric current that is conducted transversally therethrough. According to said publication, the sorbent bed temperature is raised stepwise, so that the components that are adsorbed in the bed and desorbed therefrom at different temperatures are separated from each other as the bed is regenerated. Desorption can take place into an inert gas flow or, as an alternative, the desorbed components can be removed from the bed by vacuum ventilation.

Similar equipment is introduced in the publication WO 96/09104, where the sorbent bed is used for separating components contained in a flow by heating the bed already in the adsorption step, so that the more strongly adsorbed component is maintained in the bed, whereas the less strongly adsorbed component remains in the flow penetrating the bed. Thereafter the bed is regenerated by heating it more, so that said adsorbed component is desorbed and can be removed to a cleaning flow composed of an inert gas, such as nitrogen, or extracted by vacuum ventilation. In this publication the sorbent bed is encased in a non-conductive sheath, made for instance of ceramic material, and in the adsorption and desorption steps of the bed, the heating electric current is conducted through the bed in the direction of the gas flows. As an example, the publication mentions the separation of trichloroethylene impurities from a humid air flow.

The publication WO 96/09886 likewise describes a sorbent bed made of activated carbon and adsorbing components from a flow, through which bed the flow passes in the vertical direction. For regenerating the bed, the heating, component-desorbing electric current is conducted through the bed in the horizontal direction. Because the bed material is, owing to the effect of gravity, compacted in the lower part of the bed, and thus the electric resistance of the material in the lower part of the bed is lower than in the upper part, the heating in a uniformly wide bed takes place unevenly. As a solution for this problem, the bed described in the publication is made to be downwardly expanding in the vertical direction, cf. FIG. 6 of said publication, in which case the resistance in the lower part of the bed increases.

The publication U.S. Pat. No. 7,299,711 describes an arrangement for adsorbing contaminants from a flow and for desorbing them, which arrangement functionally corresponds to the one introduced in the above described publications, but which comprises, instead of a sorbent bed made of activated carbon, an adsorbing and desorbing metal mesh or felt-like mat made of metal wire. To said mesh or mat, there is connected an analyzer for detecting components that are separated from the bed by selective desorption.

In the publication U.S. Pat. No. 4,019,021, there is described an electric heater for a liquid or gas flow, where the flow is conducted through a bed made of electroconductive material and arranged inside a tubular structure. The tubular structure and the bed contained therein are narrowed in the flowing direction in order to heat the bed material more strongly at the final end of the bed. By this arrangement, there is achieved a progressive heating of the flow, at the same time as the flow rate is increased owing to the narrowing shape of the tube, and the resident time of the flow is shortened at the final end of the bed. The purpose is to protect the heat-sensitive components contained in the flow from being broken up. The publication does not mention absorption or desorption of the components.

If a heating electric current is conducted through the sorbent bed axially, i.e. in parallel with the medium flow, from which components are absorbed or adsorbed, and/or in parallel with the washing flow, into which components are desorbed, as must be done when placing a sorbent bed in an electrically insulating tube or when encasing it in an electrically insulating sheath, the heating power in a cylindrical bed is constant along the whole length of the bed. However, when a washing flow is started, its bed-cooling effect at the first end of the bed is stronger than at the final end, and as a consequence, the final end of the bed is heated more than the first end. This in turn weakens the sharpness of the resolution of components in a bed, where the volume and heating power of the electric current conducted therethrough is gradually increased. From the hotter final end of the bed, there tend to be desorbed and washed away such components that at the cooler first end of the bed still remain attached to the bed material.

SUMMARY

The object of the present invention is to provide a solution for the above mentioned problem, which solution either partly or completely compensates the uneven heating of the bed material in a bed heated by an axially oriented electric current and washed by a flow that is heated in the bed. The device according to the invention for concentrating components contained in the flow is characterized in that in between its inlet and outlet ends, the sorbent bed is widened in the direction of the washing flow. This means that electric current at the wider outlet end of the bed is distributed on a larger quantity of bed material than at the inlet end of the bed, and generates less power per unit of volume of the bed material, which as such would lower the temperature at the outlet end of the bed with respect to the inlet end. This difference is equalized by a cool washing air flow entering the bed and being progressively heated, which washing air flow cools more strongly the inlet end of the bed, where the temperature difference between the bed material and the flow is at highest. Optimally there can in this way be obtained an essentially equal temperature along the whole length of the bed.

Respectively, as a decisive, characteristic feature of the analyzing equipment according to the invention, which equipment, apart from a porous, electroconductive sorbent bed also comprises an analyzer for detecting components, there can be defined the fact that in the direction of the washing flow, the sorbent bed expands towards that end that is located on the side of the analyzer.

The electric current penetrating the bed in the axial direction can be generated by electrodes located at the bed ends, and in order to ensure contacts, the electrode can be pressed, at least at the other end of the bed, by a spring against the bed. A narrow wire-like spring is advantageous also because it reduces the conduction of heat to the metal elements provided at the bed ends.

The equalization of the sorbent bed temperature according to the invention functions irrespective of the position of the bed. The axial direction of the bed, which also is the direction of the medium and washing flows, can thus be horizontal, inclined or vertical. From the point of view of the invention, the effect of gravity is inessential, particularly in the small-size sorbent bed of the analyzer (diameter typically only a few millimeters), where the weight of the bed material is insignificant in comparison with the spring force directed to the bed, by means of which there is achieved an essentially homogeneous electroconductivity in a particle-shaped, pneumatic or self-supportive bed material.

The encasing of a sorbent bed according to the invention in a non-conductive sheath made for instance of ceramic material is also advantageous for the overall construction of the device. The sorbent bed can be made of activated carbon, or of other corresponding grainy or extruded material, for example felt-like material made of metal wires or fibers. In shape, the bed can be for example conically widening in the flowing direction.

A method according to the invention for analyzing components contained in a flowing medium, in which method the components are absorbed or adsorbed from a medium flow into a porous, electroconductive sorbent bed and desorbed from the sorbent bed into a washing flow by heating the bed by electric current, and in which method the washing flow is conducted from the bed to an analyzer for defining the desorbed components, is characterized in that the temperature of the sorbent bed that is widened in the flowing direction is equalized in the desorption and washing step by shifting the heat in the washing flow towards the outlet end of the bed, which is located on the side of the analyzer and constitutes a wider end that is heated less by electric current. If the sorbent bed temperature is steplessly raised in the desorption and washing step, the components desorbed at different temperatures are in the analyzer curves shown as peaks clearly distinguished from each other.

BRIEF DESCRIPTION OF THE DRAWINGS

In the description below, the invention is explained with reference to a few examples and to the appended drawings, where.

DETAILED DESCRIPTION OF THE DRAWINGS

Figure 1:
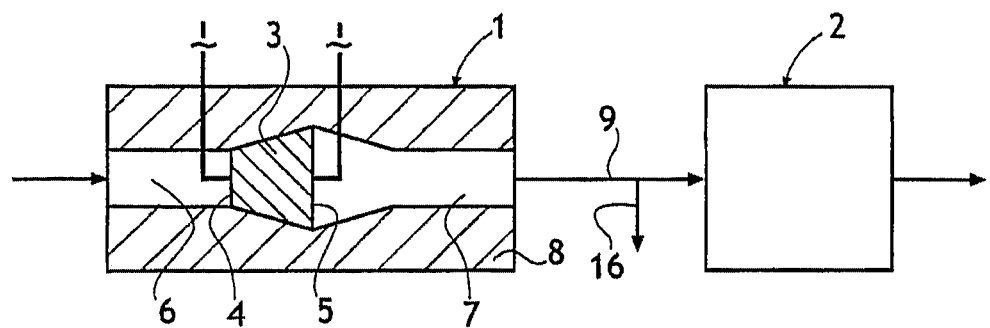
FIG. 1 is a schematical and simplified illustration of the equipment according to the invention for analyzing components contained in a flowing medium.

The analyzer equipment illustrated schematically in FIG. 1 comprises a concentrator 1 retaining components contained in a medium flow, and an analyzer 2 connected in succession thereto, to which analyzer the components can be transferred by means of a washing flow. The concentrator 1 includes a sorbent bed 3 having the shape of a truncated cone and widening in the flowing direction, said bed being formed of an inert, particle-shaped filtering medium, such as activated carbon grains. At the inlet and outlet ends 4, 5 of the sorbent bed 3, there are arranged electrodes made of for instance metal mesh for conducting electric current through the sorbent bed. The sorbent bed 3 and the connected inlet and outlet channels 6, 7 of the flow are encased in a sheath 8 made of a non-conductive, ceramic material. The analyzer 2, which is in flowing communication 9 with the outlet channel 7 of the concentrator 1, constitutes for example a gas detection device.

Figure 2:
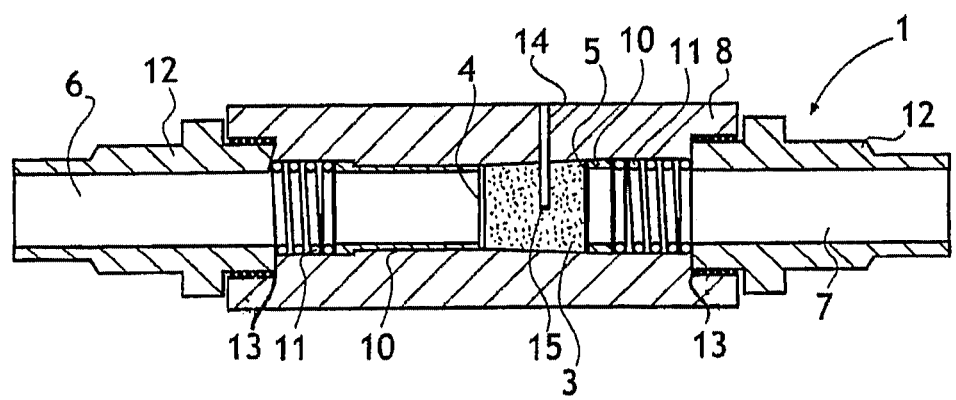
FIG. 2 is a more detailed illustration, shown in a larger scale, of the concentrator included in the equipment, as an embodiment according to the invention.

In principle the concentrator 1 that is illustrated in more detail in FIG. 2 is exactly similar to that illustrated in FIG. 1. From FIG. 2 it is seen that the metal meshes, located at the ends 4, 5 of the sorbent bed 3 made of activated carbon and serving as electrodes, are both pressed against the sorbent bed by means of a metal sleeve 10 and a spring 11 that presses the sleeve. The inlet and outlet channels 6, 7 are defined by metallic hose couplings 12, which couplings serve as electroconductors, from which the current is conducted via springs 11 and sleeves 10 to the electrodes 4, 5. The hose couplings 12 are fastened by threaded joints to a ceramic sheath 8, and Teflon sealings 13 are arranged in between the couplings and the sheath. The sheath 8 is provided with a bore 14, through which a thermocouple 15 is installed in the sorbent bed 3 for observing the temperature of the filter material. The thermocouple 15 is galvanically insulated from the heating connection of the sorbent bed 3, i.e. from the electrodes provided at the bed ends 4, 5, which prevents the passage of electric current through the thermocouple.

The equipment according to FIGS. 1 and 2 functions so that in the first step, from a flowing medium, which can be liquid or gas, there are absorbed impurities contained therein, for example organic compounds, to a sorbent bed 3, and in the next step the sorbent bed 3 is heated by electric current, at the same time as a washing flow—which can be inert gas, for instance nitrogen, or likewise air—transfers the components desorbed from the bed to the analyzer 2 for detection. Thereafter the medium flow is brought, via the inlet channel 6, to the inlet end 4 of the sorbent bed 3, and after flowing through the bed, the flow continues via the bed outlet end 5 to the outlet channel 7 and further via the outlet conduits 9, 16 out of the equipment. The components to be analyzed that have been in the medium flow are absorbed in the sorbent bed 3.

In the next analyzing step, there is started the washing flow, constituting for instance nitrogen gas, to pass from the inlet channel 6 to the sorbent bed 3 and further via the outlet channel 7 and the flow conduit 9 to the analyzer 2. To the sorbent bed 3, there is connected an electric current, which begins to heat the bed. The bed temperature is observed by a thermocouple 15, and the electric current is adjusted so that the bed is heated steplessly. Because the washing flow that enters in a cool state is heated in the sorbent bed 3, so that the temperature difference between the washing flow and the bed material is reduced towards the bed outlet end 5, also the bed-cooling effect is respectively reduced. Normally this would result in that the temperature at the bed inlet end 4 would remain lower than the temperature at the bed outlet end 5. This is, however, compensated by the conically widening shape of the bed 3, which distributes the heating power generated by the electric current on a wider area in the bed outlet end 5 than in the bed inlet end 4, and thus heats the bed material in the bed inlet end more effectively than in the outlet end. When the effects influencing the temperature of the bed 3 more or less compensate each other, an essentially homogeneous temperature in the bed can be achieved by a suitable coning angle and by adjusting the washing flow parameters.

Along with the rise in temperature that takes place in the sorbent bed 3, the components absorbed in the bed are desorbed one by one, each in the specific temperature of the component in question. The analyzer 2 observes the bed temperature measured by the thermocouple 15 and the response caused by the components as a function of time, so that the different components are distinguished as separate peaks in the curves. The more smoothly the temperature in the bed 3 rises, the better is the resolution of the analyzer 2, i.e. the sharpness of the peaks shown in the curves.

According to the specification above, the medium flow, from which impurities are absorbed in the sorbent bed 3, and the washing flow, in which impurities are desorbed, flow in parallel, in FIGS. 1 and 2 from left to right. It is, however, possible that the flows proceed in opposite directions, in which case the medium flow in the Figures would proceed from right to left, i.e. the wider end 5 of the bed 3 would serve as the inlet end, and the narrower end 4 would serve as the outlet end, and the washing flow according to the description would proceed from left to right.

The invention was tested in two comparative experiments, which are explained in the following examples 1 and 2.

EXAMPLE 1

Figure 3:
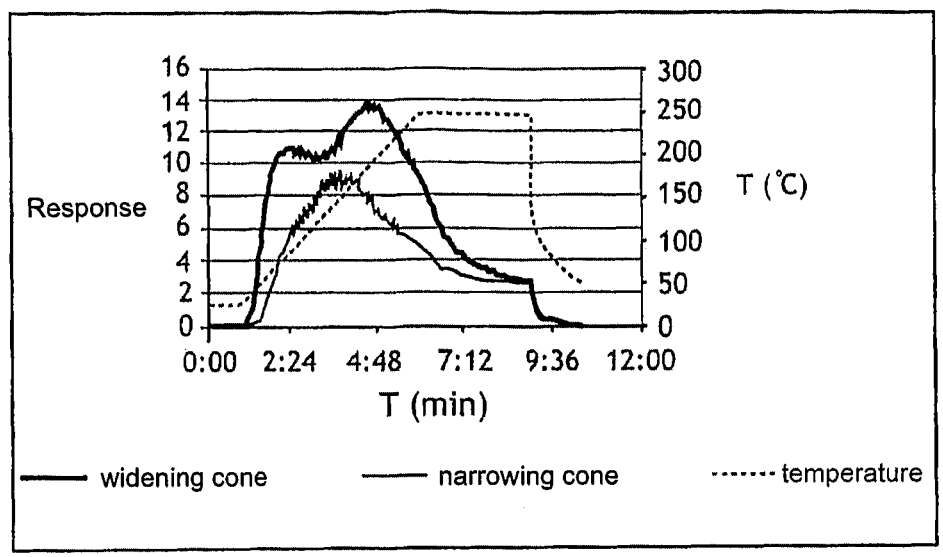
FIG. 3 is a curvature obtained in experiments for comparing concentrators, showing the responses from two different components and a steplessly rising temperature as functions of time.

This experiment studied the effect of the flowing direction in the result of analysis, when using a sorbent bed having the shape of a truncated cone. The sorbent bed was located in the concentrator first according to the invention, so that it was conically widening in the flowing direction, i.e. the narrower end of the cone served as the flow inlet end, and the wider end as the flow outlet end. The medium flow contained two absorbing components, which in the desorption step were transferred in the washing flow to the analyzer, and in the response curve measured by the analyzer they are seen as two clearly distinguished peaks, cf. the curve "widening cone" in FIG. 3. Thereafter there was carried out a comparative experiment by turning the conical sorbent bed upside down in the flowing direction, i.e. so that it was narrowed in the flowing direction. This took place simply by exchanging the inlet and outlet tubes of the concentrator in the test arrangement. In the response curve of FIG. 3 ("narrowing cone") the peaks are merged, i.e. the arrangement is, when constructed like this, left without a capacity for resolution.

EXAMPLE 2

Figure 4:
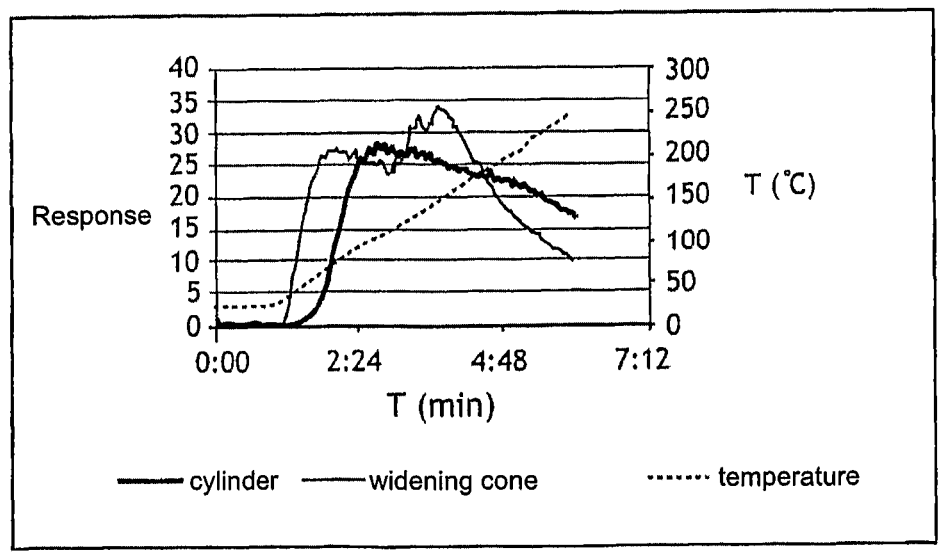
FIG. 4 illustrates, in similar fashion as FIG. 3, the curvature obtained in another comparative experiment.

In this experiment, there was carried out a comparison between a sorbent bed that is conically widening in the flowing direction and a cylindrical sorbent bed of the prior art. The experiments were carried out in the same fashion as in Example 1, and resulting response curves are shown in FIG. 4. It can be seen even in this case, with a conically widening sorbent bed according to the invention, the desorption peaks of the components are clearly distinguished, whereas with a cylindrical sorbent bed according to the prior art, the equipment is left without a capacity for resolution.

The invention claimed is:

1. A device for concentrating components contained in a flowing medium, comprising axial inlet and outlet ends of the flow, as well as a porous sorbent bed therebetween, in which sorbent bed components can be absorbed or adsorbed from a medium flow conducted through the bed, and which bed is electroconductive, so that components can be desorbed to a washing flow conducted through the bed by heating the bed with an axially directed electric current, wherein the sorbent bed is between its inlet and outlet ends widening in the direction of the washing flow.

2. A device according to claim 1, wherein the lengthwise axis between the ends of the sorbent bed is mainly horizontal.

3. A device according to claim 1, wherein the sorbent bed is conically widening in the flowing direction.

4. A device according to claim 1, wherein the sorbent bed is encased in a non-conductive sheath.

5. A device according to claim 1, wherein the sorbent bed is made of activated carbon.

6. A device according to claim 1, wherein the ends of the sorbent bed are provided with electrodes for generating the electric current passing through the bed, and that at least one end of the sorbent bed is provided with a spring for pressing the electrodes against the bed.

7. Equipment for analyzing components contained in a flowing medium, said equipment comprising a porous sorbent bed, in which components can be absorbed or adsorbed from a medium flow conducted through the bed, and which bed is electroconductive, so that components can be desorbed to a washing flow conducted by heating the bed by electric current; and an analyzer that is in flowing communication with the bed, to which analyzer the washing flow can be conducted for defining the desorbed components, wherein the sorbent bed is widening towards that end thereof that in the flowing direction is located on the side of the analyzer.

8. Equipment according to claim 7, wherein the sorbent bed is conically widening in the flowing direction.

9. Equipment according to claim 7, wherein the sorbent bed is encased in a non-conductive sheath.

10. Equipment according to claim 7, wherein the ends of the sorbent bed are provided with electrodes for generating the electric current that passes through the bed, and that at least one end of the sorbent bed is provided with a spring for pressing the electrodes against the bed.

11. Equipment according to claim 7, wherein the sorbent bed is provided with a sensor for measuring the temperature of the sorbent material, for instance with a thermocouple.

12. Equipment according to claim 11, wherein the sensor is galvanically insulated from the electroconductive sorbent material.

13. Equipment according to claim 11, wherein the measuring connection of the sensor is galvanically insulated from the heating coupling of the sorbent bed.

14. A method for analyzing components contained in a flowing medium, wherein method components are absorbed or adsorbed from a medium flow to a porous, electroconductive sorbent bed and further desorbed from the sorbent bed to a washing flow by heating the bed by electric current; wherein a washing flow is conducted from the bed to an analyzer for defining the desorbed components, wherein the temperature of the sorbent bed widening in the flowing direction is equalized in the desorption and washing step by transferring heat in the washing flow towards the wider outlet end of the bed that is located on the side of the analyzer and is less heated by electric current.

15. A method according to claim 14, wherein in the desorption and washing step, the temperature of the sorbent bed is raised steplessly.

16. A method according to claim 14, wherein sorbent bed temperature is observed, and the electric current is adjusted on the basis of the measured bed temperature.

17. A method according to claim 16, wherein the effective electric current is adjusted by pulse-width modulation.

\* \* \* \* \*